United States Patent
Lee et al.

(10) Patent No.: US 11,510,958 B2
(45) Date of Patent: Nov. 29, 2022

(54) METHOD FOR TREATING PSORIASIS

(71) Applicant: Chen-Yu Lee, Taipei (TW)

(72) Inventors: Chen-Yu Lee, Taipei (TW); Yi-De Kuo, New Taipei (TW); Hsuan-Ching Tseng, New Taipei (TW); Yan-Chih Liao, Taipei (TW); Luan-Yao Chien, Taipei (TW); Kun-Cheng Lin, New Taipei (TW); Wei-Te Cheng, New Taipei (TW)

(73) Assignee: Chen-Yu Lee, Taipei (TW)

( * ) Notice: Subject to any disclaimer, the term of this patent is extended or adjusted under 35 U.S.C. 154(b) by 146 days.

(21) Appl. No.: 17/090,931

(22) Filed: Nov. 6, 2020

(65) Prior Publication Data
US 2022/0143127 A1    May 12, 2022

(51) Int. Cl.

| | |
|---|---|
| *A61K 36/9068* | (2006.01) |
| *A61P 17/06* | (2006.01) |
| *A61K 36/65* | (2006.01) |
| *A61K 36/31* | (2006.01) |
| *A61K 36/539* | (2006.01) |
| *A61K 36/725* | (2006.01) |
| *A61K 47/02* | (2006.01) |
| *A61K 36/718* | (2006.01) |
| *A61K 36/88* | (2006.01) |
| *A61K 36/185* | (2006.01) |
| *A61K 36/736* | (2006.01) |
| *A61K 35/02* | (2015.01) |
| *A61K 36/884* | (2006.01) |
| *A61K 36/284* | (2006.01) |
| *A61K 36/61* | (2006.01) |
| *A61K 9/00* | (2006.01) |

(52) U.S. Cl.
CPC ........ *A61K 36/9068* (2013.01); *A61K 9/0019* (2013.01); *A61K 9/0053* (2013.01); *A61K 35/02* (2013.01); *A61K 36/185* (2013.01); *A61K 36/284* (2013.01); *A61K 36/31* (2013.01); *A61K 36/539* (2013.01); *A61K 36/61* (2013.01); *A61K 36/65* (2013.01); *A61K 36/718* (2013.01); *A61K 36/725* (2013.01); *A61K 36/736* (2013.01); *A61K 36/88* (2013.01); *A61K 36/884* (2013.01); *A61K 47/02* (2013.01); *A61P 17/06* (2018.01)

(58) Field of Classification Search
None
See application file for complete search history.

(56) References Cited

U.S. PATENT DOCUMENTS

| | | | | |
|---|---|---|---|---|
| 5,466,452 A | * | 11/1995 | Whittle | ......... A61K 36/65 514/858 |
| 2016/0361261 A1 | * | 12/2016 | Carpanzano | ......... A61K 9/1652 |

OTHER PUBLICATIONS

Chen, K., et al., Literature Research of Chinese Medical Syndromes and Prescription Drug Law of Psoriasis (2012), available at https://citeseerx.ist.psu.edu/viewdoc/download?doi=10.1.1.636.1438&rep=rep1&type=pdf, accessed May 26, 2022.*

* cited by examiner

*Primary Examiner* — H. Sarah Park
(74) *Attorney, Agent, or Firm* — Bacon & Thomas, PLLC

(57) ABSTRACT

The present invention relates to a method for treating psoriasis including: administering a Chinese medicine composition to a subject in need thereof; wherein the Chinese medicine composition is an extract of a first mixture including *Pimenta officinalis, Paeonia veitchii, Anastatica hierochuntica, Zingiber officinale, Scutellaria baicalensis,* and *Ziziphus jujube.*

18 Claims, No Drawings

METHOD FOR TREATING PSORIASIS

BACKGROUND OF THE INVENTION

1. Field of the Invention

The present invention relates to a method for treating psoriasis.

2. Description of Related Art

Due to the potential of Chinese herbal medicine for treating cancer, traditional Chinese herbal medicine has gradually attracted attention in recent years. The principle of applying Chinese herbal medicine is based on the practice of traditional Chinese medicine theory.

Psoriasis is a chronic skin disease caused by the immune system attacking skin cells, and its main symptom includes abnormal skin of redness, itchiness and peeling. In addition, psoriasis is also considered as a genetic disease induced by environmental factors. Normally, it is more severe in winter or when the patient takes certain drugs, and the patient's mental state may also affect the disease.

At present, there is no cure for psoriasis, and known treatments can only control the disease. The treatments include the use of steroid ointment, UV phototherapy, immunosuppressive agent and the like. Therefore, there is an urgent need to provide a new treatment to patients with psoriasis to alleviate the condition of patients with psoriasis or improve their quality of life.

SUMMARY OF THE INVENTION

The present invention relates to a composition and method for treating psoriasis, which can alleviate psoriasis in patients or improve their quality of life.

The present invention provides a Chinese medicine composition for treating psoriasis, and the Chinese medicine composition comprises an extract of a first mixture comprising *Pimenta officinalis*, *Paeonia veitchii*, *Anastatica hierochuntica*, *Zingiber officinale*, *Scutellaria baicalensis*, and *Ziziphus jujube*.

The present invention further provides a method fir treating psoriasis, comprising: administering said Chinese medicine composition to a subject in need thereof. Specifically, an effective amount of said Chinese medicine composition is administered to the subject in need thereof.

The Chinese medicine composition may be prepared by the following steps: providing the first mixture; mixing the first mixture with water to form a second mixture; heating the second mixture to obtain a crude extract; and filtering the crude extract to keep a liquid extract and obtain the Chinese medicine composition.

The first mixture of the present invention may comprise 4-6 parts by weight of *Pimenta officinalis*, 4-6 parts by weight of *Paeonia veitchii*, 4-6 parts by weight of *Anastatica hierochuntica*, 4-6 parts by weight of *Zingiber officinale*, 2-30 parts by weight of *Scutellaria baicalensis*, and 4-6 parts by weight of *Ziziphus jujube*.

The first mixture of the present invention may further comprise at least one ingredient selected from the group consisting of *Ephedra sinica*, *Prunus armeniaca*, *Coix lacryma-jobi*, *Gypsum fibrosum*, *Asparagus cochinchinensis*, *Fructus liquidambaris*, *Atractylodes lancea*, *Alisma plantago-aquatica*, talcum, *Coptis teeta*, *Ophiopogon japonicus*, *Tribulus terrestris*, and *Gleditsia sinensis*.

The first mixture of the present invention may further comprise at least one ingredient selected from the group consisting of 2-4 parts by weight of *Ephedra sinica*, 3-5 parts by weight of *Prunus armeniaca*, 3-9 parts by weight of *Coix lacryma-jobi*. 9-11 parts by weight of *Gypsum fibrosum*, 7-9 parts by weight of *Asparagus cochinchinensis*, 8-12 grains of *Fructus liquidambaris*, 4-6 parts by weight of *Atractylodes lancea*, 4-6 parts by weight of *Alisma plantago-aquatica*, 4-16 parts by weight of talcum, 7-16 parts by weight of *Coptis teeta*, 7-9 parts by weight of *Ophiopogon japonicus*, 9-11 parts by weight of *Tribulus terrestris*, and 4-6 parts by weight of *Gleditsia sinensis*.

The first mixture of the present invention may further comprise *Ephedra sinica*, *Prunus armeniaca*, *Coix lacryma-jobi*, *Gypsum fibrosum*, *Asparagus cochinchinensis*, *Fructus liquidambaris*, *Atractylodes lancea*, and *Alisma plantago-aquatica*. In one aspect of the present invention, the first mixture may further comprise 2-4 parts by weight of *Ephedra sinica*, 3-5 parts by weight of *Prunus armeniaca*, 3-9 parts by weight of *Coix lacryma-jobi*, 9-11 parts by weight of *Gypsum fibrosum*, 7-9 parts by weight of *Asparagus cochinchinensis*, 9-11 grains of *Fructus liquidambaris*, 4-6 parts by weight of *Atractylodes lancea*, and 4-6 parts by weight of *Alisma plantago-aquatica*.

The first mixture of the present invention may further comprise talcum. In one aspect of the present invention, the first mixture may further comprise 4-16 parts by weight of talcum.

The first mixture of the present invention may further comprise *Coptis teeta*. In one aspect of the present invention, the first mixture may further comprise 9-16 parts by weight of *Coptis teeta*.

The first mixture of the present invention may further comprise *Ophiopogon japonicus*. In one aspect of the present invention, the first mixture may further comprise 7-9 parts by weight of *Ophiopogon japonicus*.

The first mixture of the present invention may further comprise *Ephedra sinica*, *Prunus armeniaca*, *Coix lacryma-jobi*, *Gypsum fibrosum*, *Asparagus cochinchinensis*, *Atractylodes lancea*, *Alisma plantago-aquatic*, talcum, *Coptis teeta*, *Ophiopogon japonicas*, and *Tribulus terrestris*. In one aspect of the present invention, the first mixture may further comprise 2-4 parts by weight of *Ephedra sinica*, parts by weight of *Prunus armeniaca*, 3-5 parts by weight of *Coix lacryma-jobi*, 9-11 parts by weight of *Gypsum fibrosum*, 7-9 parts by weight of *Asparagus cochinchinensis*, 4-6 parts by weight of *Atractylodes lancea*, 4-6 parts by weight of *Alisma plantago-aquatic*, 4-6 parts by weight of talcum, 14-16 parts by weight of *Coptis teeta*, 7-9 parts by weight of *Ophiopogon japonicas*, and 9-11 parts by weight of *Tribulus terrestris*.

The first mixture of the present invention may further comprise *Ephedra sinica*, *Prunus armeniaca*, *Gypsum fibrosum*, *Asparagus cochinchinensis*, *Fructus liquidambaris*, *Atractylodes lancea*, *Alisma plantago-aquatic*, talcum, *Coptis teeta*, *Ophiopogon japonicas*, *Tribulus terrestris*, and *Gleditsia sinensis*. In one aspect of the present invention, the first mixture may further comprise 2-4 parts by weight of *Ephedra sinica*, 3-5 parts by weight of *Prunus armeniaca*, 9-11 parts by weight of *Gypsum fibrosum*, 7-9 parts by weight of *Asparagus cochinchinensis*, 9-11 grains of *Fructus liquidambaris*, 4-6 parts by weight of *Atractylodes lancea*, 4-6 parts by weight of *Alisma plantago-aquatic*, 4-6 parts by weight of talcum, 7-9 parts by weight of *Coptis teeta*, 7-9 parts by weight of *Ophiopogon japonicas*, 9-11 parts by weight of *Tribulus terrestris*, and 4-6 parts by weight of *Gleditsia sinensis*.

In the present invention, the part by weight of the first mixture may be 2.5-5 gram per part, preferably 3-4 gram per part, more preferably 3.75 gram per part, but the present invention is not limited thereto.

In the present invention, the term "treat" or "treatment" used herein refers to administer a Chinese medicine composition of the present invention to a subject in need thereof, thereby inhibiting, curing, improving, healing, ameliorating, alleviating, changing, or affecting a disease or the tendency of a disease.

In the present invention, the term "effective amount" used herein refers to a necessary dose leading to expected therapeutic effects in a subject treated, and it may be adjusted depending on the route of administration, the use of excipients and the combined use with other medicaments.

The Chinese medicine composition of the present invention may be administered via oral administration or injection.

The Chinese medicine composition of the present invention may further comprise pharmaceutically acceptable carrier, stabilizer, thinner, dispersant, suspending agent, thickener, excipient or the combination thereof.

In the present invention, the term "acceptable" used herein means that it should be compatible with the Chinese medicine composition, preferably be able to stabilize the Chinese medicine composition, and cannot jeopardize the subject treated.

The present invention is not restrictive of the method for decocting Chinese medicine, and it can be implemented in any known manner. The present invention is not restrictive of the method for heating the Chinese medicine, and it can be implemented by any known method, such as direct heating and double-boiling.

DETAILED DESCRIPTION OF THE PREFERRED EMBODIMENT

The following embodiments are meant to explain the implementation of the present invention, they should be construed as descriptive merely, and should not restrict the remaining part of the present invention. The person having ordinary skills in the art can easily understand other advantages and effects of the present invention. The present invention may also be implemented or applied by other different embodiments, and various details in this specification may also be modified and changed according to different viewpoints and applications without departing from the spirit of the invention.

Unless specified otherwise, all technical and scientific terms described in the specification and claims of the present invention are defined as follows. In the present invention, singular terms, "the" or "said" may refer to one or more objects, unless specified otherwise. In addition, the term "comprise" is an open-ended transition word which does not limit to the items listed. The foregoing paragraphs are only systematic references and should not be construed as limitations for the subject of the invention. Unless specified otherwise, the materials used in the present invention are commercially available and easy to obtain. Possible sources for obtaining the materials are listed below and it is exemplary only.

In the following preparation examples, the part by weight is 3.75 gram per part.

Preparation Example 1

Provide 5 parts by weight of *Pimenta officinalis*, 5 parts by weight of *Paeonia veitchii*, 5 parts by weight of *Anastatica hierochuntica*, 5 parts by weight of *Zingiber officinale*, 3 parts by weight of *Scutellaria baicalensis*, and 5 parts by weight of *Ziziphus jujube* to form a first mixture-1; mix the first mixture-1 with 2000 ml of water to form a second mixture-1; decoct the second mixture-1 for 1 hour to form about 500-600 ml of a crude extract; filter the crude extract and collect the filtrate to obtain a Chinese medicine composition-1 of the present preparation example.

Preparation Example 2

The first mixture-1 of Preparation Example 1 was added with 3 parts by weight of *Ephedra sinica*, 4 parts by weight of *Prunus armeniaca*, 8 parts by weight of *Coix lacryma-jobi* 10 parts by weight of *Gypsum fibrosum*, 8 parts by weight of *Asparagus cochinchinensis*, 10 grains of *Fructus liquidambaris*, 5 parts by weight of *Atractylodes lancea*, 5 parts by weight of *Alisma plantago-aquatic*, 8 parts by weight of *Scutellaria baicalensis* to form a first mixture-2. Then, extract the first mixture-2 in a manner similar to Preparation Example 1 to obtain a Chinese medicine composition-2 of the present preparation example.

Preparation Example 3

The first mixture-2 of Preparation Example 2 was added with 7 parts by weight of *Scutellaria baicalensis* to form a first mixture-3. Then, extract the first mixture-3 in a manner similar to Preparation Example 1 to obtain a Chinese medicine composition-3 of the present preparation example.

Preparation Example 4

The first mixture-3 of Preparation Example 3 was added with 5 parts by weight of *Scutellaria baicalensis* and 8 parts by weight of talcum to form a first mixture-4. Then, extract the first mixture-4 in a manner similar to Preparation Example 1 to obtain a Chinese medicine composition-4 of the present preparation example.

Preparation Example 5

The first mixture-4 of Preparation Example 4 was added with 5 parts by weight of *Scutellaria baicalensis* and 7 parts by weight of talcum to form a first mixture-5. Then, extract the first mixture-5 in a manner similar to Preparation Example 1 to obtain a Chinese medicine composition-5 of the present preparation example.

Preparation Example 6

The first mixture-3 of Preparation Example 3 was added with 15 parts by weight of talcum and 10 parts by weight of *Coptis teeta* to form a first mixture-6. Then, extract the first mixture-6 in a manner similar to Preparation Example 1 to obtain a Chinese medicine composition-6 of the present preparation example.

Preparation Example 7

The first mixture-1 of Preparation Example 1 was added with 3 parts by weight of *Ephedra sinica*, 4 parts by weight of *Prunus armeniaca*, 4 parts by weight of *Coix lacryma-jobi*, 10 parts by weight of *Gypsum fibrosum*, 8 parts by weight of *Asparagus cochinchinensis*, 10 grains of *Fructus liquidambaris*, 5 parts by weight of *Atractylodes lancea*, 5 parts by weight of *Alisma plantago-aquatic*, 10 parts by weight of *Scutellaria baicalensis*, 5 parts by weight of talcum, 15 parts by weight of *Coptis teeta*, and 8 parts by weight of *Ophiopogon japonicus* to form a first mixture-7. Then, extract the first mixture-7 in a manner similar to Preparation Example 1 to obtain a Chinese medicine composition-7 of the present preparation example.

Preparation Example 8

The first mixture-1 of Preparation Example 1 was added with 3 parts by weight of *Ephedra sinica*, 4 parts by weight of *Prunus armeniaca*, 4 parts by weight of *Coix lacryma-jobi*, 10 parts by weight of *Gypsum fibrosum*, 8 parts by weight of *Asparagus cochinchinensis*, 5 parts by weight of *Atractylodes lancea*, 5 parts by weight of *Alisma plantago aquatica* 15 parts by weight of *Scutellaria baicalensis*, 5 parts by weight of talcum, 15 parts by weight of *Coptis teeta*, 8 parts by weight of *Ophiopogon japonicas*, and 10 parts by weight of *Tribulus terrestris* to form a first mixture-8. Then, extract the first mixture-8 in a manner similar to Preparation Example 1 to obtain a Chinese medicine composition-8 of the present preparation example.

Preparation Example 9

The first mixture-1 of Preparation Example 1 was added with 3 parts bye weight of *Ephedra sinica*, 4 parts bye weight of *Prunus armeniaca*, parts bye weight of *Gypsum fibrosum*, 8 parts bye weight of *Asparagus cochinchinensis*, 10 grains of *Fructus liquidambaris*, 5 parts bye weight of *Atractylodes lancea*, 5 parts bye weight of *Alisma plantago-aquatica* 8 parts bye weight of *Scutellaria baicalensis*, 5 parts bye weight of talcum, 8 parts bye weight of *Coptis teeta*, 8 parts bye weight of *Ophiopogon japonicas*, 10 parts bye weight of *Tribulus terrestris*, and 5 parts bye weight of *Gleditsia sinensis* to form a first mixture-9. Then, extract the first mixture-9 in a manner similar to Preparation Example 1 to obtain a. Chinese medicine composition-9 of the present preparation example.

Example 1

The patient with psoriasis in Example 1 had raised rashes founded in multiple locations throughout the body and being spot-like or disc-like with the size larger than a finger pad. The patient felt pain and the rash produces exudate when scratching the rashes lightly. In addition, the patient's palms, fingers, and heels were dried and cracked with cracks deep into the muscles such that the patient had to wear latex gloves for a long period of time to keep moisture.

A treatment of the present invention applied to the patient of Example 1 was described below. From the day 1, a daily dose of the Chinese medicine composition-2 was administered to the patient once a day. A follow-up report indicated that the area of psoriasis in the patient significantly reduced, and the rash red spots were rare.

Example 2

The patient of Example 2 was a patient with psoriasis. A treatment of the present invention applied to the patient of Example 2 was described below. From the day 1, a daily dose of the Chinese medicine composition-3 was administered to the patient once a day. A follow-up report indicated that the patient's fingers were still dried and cracked, but the rashes of psoriasis were no longer existent.

Example 3

The patient of Example 3 was a patient with psoriasis. A treatment of the present invention applied to the patient of Example 3 was described below From the day 1, a daily dose of the Chinese medicine composition-4 was administered to the patient once a day. A follow-up report indicated that the patient's fingers were not dried and cracked.

Example 4

The patient of Example 4 was a patient with psoriasis. A treatment of the present invention applied to the patient of Example 4 was described below. From the day 1, a daily dose of the Chinese medicine composition-5 was administered to the patient once a day. A follow-up report indicated that the psoriasis in the patient was alleviated mostly, and the locally affected area was itchy.

Example 5

The patient of Example 5 was a patient with psoriasis. A treatment of the present invention applied to the patient of Example 5 was described below. From the day 1, a daily dose of the Chinese medicine composition-6 was administered to the patient once a day. A follow-up report indicated that the patient no longer developed the rash.

Example 6

The patient of Example 6 was a patient with psoriasis. A treatment of the present invention applied to the patient of Example 6 was described below. From the day 1, a daily dose of the Chinese medicine composition-7 was administered to the patient once a day, A follow-up report indicated that the affected area of the patient was back to normal.

Example 7

The patient of Example 7 was a patient with psoriasis. A treatment of the present invention applied to the patient of Example 7 was described below. From the day 1, a daily dose of the Chinese medicine composition-8 was administered to the patient once a day, A follow-up report indicated that 90% of psoriasis in the patient was recovered.

Example 8

The patient of Example 8 was a patient with psoriasis. A treatment of the present invention applied to the patient of Example 8 was described below. From the day 1, a daily dose of the Chinese medicine composition-9 was administered to the patient once a day. A follow-up report indicated that the psoriasis in the patient was alleviated completely.

Although the present invention has been explained in relation to its preferred embodiment, it is to be understood that many other possible modifications and variations can be made without departing from the spirit and scope of the invention as hereinafter claimed.

What is claimed is:
1. A method for treating psoriasis comprising:
providing a first mixture, wherein the first mixture comprises 4-6 parts by weight of *Pimenta officinalis*, 4-6 parts by weight of *Paeonia veitchii*, 4-6 parts by weight of *Anastatica hierochuntica*, 4-6 parts by weight of *Zingiber officinale*, 2-30 parts by weight of *Scutellaria baicalensis*, and 4-6 parts by weight of *Ziziphus jujube*;

mixing the first mixture with water to form a second mixture;

heating the second mixture to obtain a crude extract;

filtering the crude extract to keep a liquid extract and obtain a Chinese medicine composition; and administering the Chinese medicine composition to a subject in need thereof.

2. The method of claim 1, wherein the part by weight of the first mixture is 2.5-5 gram per part.

3. The method of claim 1, wherein the first mixture further comprises at least one ingredient selected from the group consisting of *Ephedra sinica, Prunus armeniaca, Coix lacryma-jobi, Gypsum Fibrosum, Asparagus cochinchinensis, Fructus liquidambaris, Atractylodes lancea, Alisma plantago-aquatica*, talcum, *Coptis teeta, Ophiopogon japonicus, Tribulus terrestris*, and *Gleditsia sinensis*.

4. The method of claim 3, wherein the first mixture further comprises at least one ingredient selected from the group consisting of 2-4 parts by weight of *Ephedra sinica*, 3-5 parts by weight of *Prunus armeniaca*, 3-9 parts by weight of *Coix lacryma-jobi*, 9-11 parts by weight of *Gypsum Fibrosum*, 7-9 parts by weight of *Asparagus cochinchinensis*, 8-12 grains of *Fructus liquidambaris*, 4-6 parts by weight of *Atractylodes lancea*, 4-6 parts by weight of *Alisma plantago-aquatica*, 4-16 parts by weight of talcum, 7-16 parts by weight of *Coptis teeta*, 7-9 parts by weight of *Ophiopogon japonicus*, 9-11 parts by weight of *Tribulus terrestris*, and 4-6 parts by weight of *Gleditsia sinensis*.

5. The method of claim 4, wherein the part by weight of the first mixture is 2.5-5 gram per part.

6. The method of claim 1, wherein the first mixture further comprises *Ephedra sinica, Prunus armeniaca, Coix lacryma-jobi, Gypsum Fibrosum, Asparagus cochinchinensis, Fructus liquidambaris, Atractylodes lancea*, and *Alisma plantago-aquatica*.

7. The method of claim 6, wherein the first mixture further comprises talcum.

8. The method of claim 7, wherein the first mixture further comprises *Coptis teeta*.

9. The method of claim 8, wherein the first mixture further comprises *Ophiopogon japonicus*.

10. The method of claim 1, wherein the first mixture further comprises *Ephedra sinica, Prunus armeniaca, Coix lacryma-jobi, Gypsum Fibrosum, Asparagus cochinchinensis, Atractylodes lancea, Alisma plantago-aquatic*, talcum, *Coptis teeta, Ophiopogon japonicas*, and *Tribulus terrestris*.

11. The method of claim 1, wherein the first mixture further comprises *Ephedra sinica, Prunus armeniaca, Gypsum Fibrosum, Asparagus cochinchinensis, Fructus liquidambaris, Atractylodes lancea, Alisma plantago-aquatic*, talcum, *Coptis teeta, Ophiopogon japonicas, Tribulus terrestris*, and *Gleditsia sinensis*.

12. The method of claim 1, wherein the first mixture further comprises 2-4 parts by weight of *Ephedra sinica*, 3-5 *Prunus armeniaca*, 3-9 *Coix lacryma-jobi*, 9-11 *Gypsum Fibrosum*, 7-9 parts by weight of *Asparagus cochinchinensis*, 9-11 grains of *Fructus liquidambaris*, 4-6 parts by weight of *Atractylodes lancea*, and 4-6 parts by weight of *Alisma plantago-aquatic*.

13. The method of claim 12, wherein the first mixture further comprises 4-16 parts of talcum.

14. The method of claim 13, wherein the first mixture further comprises 9-16 parts by weight of *Coptis teeta*.

15. The method of claim 14, wherein the first mixture further comprises 7-9 parts by weigh of *Ophiopogon japonicas*.

16. The method of claim 1, wherein the first mixture further comprises 2-4 parts by weight of *Ephedra sinica*, 3-5 parts by weight of *Prunus armeniaca*, 3-5 parts by weight of *Coix lacryma-jobi*, 9-11 parts by weight of *Gypsum Fibrosum*, 7-9 parts by weight of *Asparagus cochinchinensis*, 4-6 parts by weight of *Atractylodes lancea*, 4-6 parts by weight of *Alisma plantago-aquatic*, 4-6 parts by weight of talcum, 14-16 parts by weight of *Coptis teeta*, 7-9 parts by weight of *Ophiopogon japonicas*, and 9-11 parts by weight of *Tribulus terrestris*.

17. The method of claim 1, wherein the first mixture further comprises 2-4 parts by weight of *Ephedra sinica*, 3-5 parts by weight of *Prunus armeniaca*, 9-11 parts by weight of *Gypsum Fibrosum*, 7-9 parts by weight of *Asparagus cochinchinensis*, 9-11 grains of *Fructus liquidambaris*, 4-6 parts by weight of *Atractylodes lancea*, 4-6 parts by weight of *Alisma plantago-aquatic*, 4-6 parts by weight of talcum, 7-9 parts by weight of *Coptis teeta*, 7-9 parts by weight of *Ophiopogon japonicas*, 9-11 parts by weight of *Tribulus terrestris*, and 4-6 parts by weight of *Gleditsia sinensis*.

18. The method of claim 1, wherein the Chinese medicine composition is administered via oral administration or injection.

\* \* \* \* \*